United States Patent [19]

Strauss et al.

[11] 4,357,353
[45] Nov. 2, 1982

[54] PROCESS FOR THE PRODUCTION OF AN EMULSIFIER BASED ON LECITHIN AND PRODUCT THEREOF

[75] Inventors: Kuno Strauss, Hamburg; Alice Nasner, Aumühle, both of Fed. Rep. of Germany

[73] Assignee: Lucas Meyer GmbH & Co., Hamburg, Fed. Rep. of Germany

[21] Appl. No.: 212,211

[22] Filed: Dec. 2, 1980

[30] Foreign Application Priority Data

Dec. 3, 1979 [DE] Fed. Rep. of Germany ....... 2948607

[51] Int. Cl.$^3$ ............................................ A61K 47/00

[52] U.S. Cl. ...................................... 424/365; 424/199
[58] Field of Search ................. 424/365, 199; 260/403

[56] References Cited

U.S. PATENT DOCUMENTS 4,005,190  1/1977  Mader et al. .................... 424/199 X
4,252,793  2/1981  Altman .............................. 424/199

Primary Examiner—Sam Rosen

[57] ABSTRACT

The invention relates to a process for the preparation of an emulsifier from lecithin base by solvent extraction followed by precipitation.

12 Claims, 1 Drawing Figure

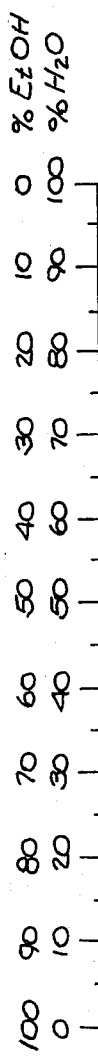

PROCESS FOR THE PRODUCTION OF AN EMULSIFIER BASED ON LECITHIN AND PRODUCT THEREOF

The instant invention relates to a process for the preparation of an emulsifier from lecithin base by solvent extraction, and to the emulsifier from lecithin base obtained by such process, as well as the use thereof in fat emulsions for intravenous administration.

Lecithins are phospholipid mixtures and present a group of natural substances accompanying fats in a great variety of mixtures of molecularly defined individual lipides. Such phospholipids are widely used as emulsifiers for different purposes, in particular in medicines and foods.

While crude phospholid mixtures, e.g. crude lecithin of the soybean which is obtained in great quantities when removing the mucilage from soybean oil as a partial step in refining the fat, are regarded as waste products, fractionating the crude lecithin improves the value thereof, and the product may be used for different purposes, depending on its composition. The fractionation partly consists of enriching certain components and partly of eliminating undesired secondary components.

Fractionating so far met with considerable technical difficulties because of the great variety of components which have physical properties that are in part very different and in part very similar.

Attempts to separate or fractionate the substances contained in lecithin or in the phospholipid mixtures by virtue of their different solubilities in certain solvents practically did not meet with success so far since the individual lipides of the phospholipid complex greatly influence one another in their solubility. It is known from U.S. Pat. No. 2,090,537 to produce hydrated lecithin from crude lecithin by solvent fractionation. However, essentially this amounts to no more than a removal of fat, while the composition of the fractionated product still is extremely complex. The hydrated form of the lecithin obtained is not suitable for many applications, in particular in the pharmaceutical field.

Further fractionating is achieved by adsorptive fractionation of the phospholipid complex on adsorbents, such as $Al_2O_3$, $MgO$, $MgCO_3$ and activated carbon. What is obtained specifically is an enrichment of phosphatidylcholine (Pc).

Methods of this kind are known from DT-AS No. 1 777 772 and 1 053 299 and from the publication in J. Biol. Chem. 192 (1951), page 623.

A distinct disadvantage of these methods is the loss of adsorbates since a quantitative desorption is not achieved, and thus also the renewed use of the expensive absorbents is at least restricted.

It is another disadvantage of the adsorption processes that there can be no separation of non-polar impurities. Among the non-polar impurities there are, above all, the accompanying fats. As regards the procedural technique, adsorption methods are characterized by the need for subsequent fine filtration and this can be a very costly process step, especially in the production in connection with GMP. These industrially exploited processes have the further disadvantage that they are suitable for discontinuous operation only.

Is it also known to fractionate phospholipid mixtures by chromatographic separating methods with which, however, again different adsorbents must be used and with which different adsorption-desorption balances of the components of the mixture are utilized for the fractionation. Although semi- or fully continuous chromatographic separating processes have become known in this context, they can be applied only if a quantitative desorption is achieved, which is not the case with the phospholipids for the above mentioned reasons. Moreover, operation at greater rates of flow and in greater units is impossible especially with column chromatography so that it is practically limited to the laboratory scale.

It is the object of the invention to provide a process by which phospholipid mixtures can be fractionated commercially, i.e. without great technical expenditure in continuous operation and with the smallest possible number of process steps, recovering a product which is suitable as an emulsifier in fat emulsions for intravenous administration.

It was found that in accordance with the invention the desired product can be obtained by filtering or centrifuging, subjecting a solution of a certain starting lecithin, which is soluble in alcohol, in a mixture of alcohol and water, with a certain alcohol:water ratio, to solvent fractionation.

Surprisingly, it was discovered that separation into different phases is obtained if a certain ratio between alcohol and water is observed in the solvent mixture, i.e. within certain mixture limits in the solvent. And a lecithin component which is not soluble in the solvent mixture mentioned is separated as a finely disperse precipitate or as an emulsion. If the precipitate is formed, separation by gravity such as centrifuging is possible, whereas in the case of the formation of an emulsion, the separation cannot be effected by gravity. In both cases, however, phase separation by filtration is possible, in particular by ultrafiltration. With emulsions this is the only possible separation.

The fractionation of phospholipid mixtures or lecithins by solvent extraction permitted by the invention, as well as the separation thus made possible of the resulting unsoluble phase by gravity or filtration is surprising because the molecular weights of the main components of the lecithin lie within the same range as those of the accompanying fats, namely approximately between 700 and 900 so that successful fractionating of the principal components of lecithin by filtration seemed to have no chances of success. True, it was known that lecithin and water form association complexes of different structure depending on the chemical properties of the individual phospholipids, the molar composition of the lecithin, the concentration in the aqueous solution, and the temperature. Yet it could not be expected either that fractionating lecithin by way of such association complexes would be possible since the individual phospholipids of the lecithin jointly take part in the structure of these complexes, a fact also demonstrated by their mutual influence on the solubility. For the above reasons the use of filtration, including ultrafiltration has not been attempted so far or not been realizable with success for cleaning and fractionating phospholipids.

In accordance with the invention the solvent extraction and separation of the desired product are made possible in particularly simple manner, the criterion being the adjustment of a certain ratio between alcohol and water in the solvent mixture consisting of these two components.

A solution of a phospholipid mixture in alcohol is started from according to the invention and water in certain quantities is added.

It was found that when adding water to an alcoholic solution of egg lecithin in an amount of from 35 to 65%, based on the resulting solvent mixture, immediate flocculation of an unsoluble phase takes place. This unsoluble phase can be isolated by centrifuging or filtering, e.g. by ultrafiltration. It has also been discovered that the product thus obtained is so rich in phosphatidylcholine (Pc) and already contains a suitable ratio between phosphatidylcholine and phosphatidylethanolamine (Pe) that it is suitable as an emulsifier in fat emulsions intended for artificial feeding by intravenous administration.

According to another embodiment of the invention water in an amount of from 5 to 65%, based on the resulting solvent mixture, is added to a solution of egg lecithin in alcohol. Also in this case a phase separation takes place. When adding water in an amount of from 5 to 35%, based on the resulting solvent mixture, a phase separation takes place after a long a period of rest, i.e. after about 12 hours, for example over night.

According to another embodiment of the invention water in an amount of from 65 to 96%, based on the resulting solvent mixture, is added to an alcoholic solution of soybean lecithin whereupon flocculation of the unsoluble phospholipid proportion takes place at once. This product can also be separated easily by gravity, e.g. by centrifuging or by filtration, such as ultrafiltration. The product also has the above mentioned desirable properties.

In accordance with yet another embodiment of the invention water in an amount of from 5 to 55%, based on the resulting solvent mixture, is added to an alcoholic solution of soybean lecithin. In this case the phase separation takes place after letting the mixture rest for about 12 hours, e.g. over night, whereupon the separation may be effected. The resulting product likewise has the desired properties.

The embodiment possibilities of the invention explained above are demonstrated graphically in the table as shown in the drawings.

Where phase separation takes place by the formation of an emulsion with some embodiments of the invention, of course, the separation cannot be effected by means of gravity, such as centrifuging. In this case, however, separation by filtration can be effected, and ultrafiltration is provided in particular.

Equipment of conventional structure can be used for the ultrafiltration. Of the known structures, an ultrafiltration means of the flat membrane module type is particularly preferred because, among others, it has the advantage of permitting individual removal of the permeating substance from each membrane and thus convenient control of the membrane function. Moreover, a series connection of the membranes permits low repumping rates. Celluloseacetate, polyacrylonitrile, polyamide, and polysulfons have proved to be suitable membrane materials.

The following advantages are obtained when applying the ultrafiltration for separating the product to be prepared:

1. The arrangement is characterized by a high degree of efficiency.
2. The arrangement can be operated by process control, including a cleaning cycle so that a considerable amount of time is saved in comparison with the adsorption process.
3. The arrangement can be built as a completely closed system so that among others it fulfills the requirements regarding sterility, regardless of the hygienic conditions of the working space.
4. The number of process step is smaller than in the case of an adsorption method.
5. The process conditions and thus the production properties are variable within wide limits without requiring any apparatus measures.
6. The manufacturing costs are reduced since no adjuvants (apart from the solvent circulating in the process) are required, no product loss occurs due to non-recoverable fractions, automatic plant control is possible, and better quality of the product as well as better uniformity of the product quality are achieved.

The product obtained according to the invention either by centrifuging or by filtering subsequently is dried in vacuum, excluding oxygen, preferably by way of freeze-drying. The product then obtained has a maximum fat content of 3%, preferably no more than 2%.

The product obtained by the method of the invention has the following physico-chemical parameters:

1. ratio between Pc and Pe from 7:3 to 6:1, preferably 4:1,
2. Pc content from 65 to 85% by weight, preferably from 75 to 80% by weight,
3. residual fat content less than 2%,
4. pyrogen-free in the rabbit test according to the European Pharmacopoeia (1975) vol. 2, page 56 et seqq.,
5. clearly soluble in ethanol at 5% concentration,
6. clearly soluble in chloroform at 10% concentration,
7. maximum water content 2.5%, preferred maximum 1%,
8. maximum peroxide number 5, preferred maximum 1 (determined according to the DGF standard method F-I 3b (68).

The product (emulsifier) obtained by the process of the invention further must fulfill the following conditions:

(a) The emulsifier must not be toxic.
(b) The emulsifier must be free of pyrogenic impurities.
(c) The emulsifier must permit the formation of a finely disperse emulsion having a shelf life of more than 2 years.
(d) The emulsifier must be adapted to be sterilized in the emulsion, i.e. it must be heatable to the sterilization temperature without decomposing.

The requirements to be fulfilled by a product which is suitable for artificial feeding by intravenous administration are described in the book "The Pathology of Parenteral Nutrition with Lipids" by Samuel Wesley Thompson, published by Charles C. Thomas, Springfield, Illinois, U.S.A., cf. pages 14–16. It follows from this publication that extremely high requirements must be fulfilled with respect to the purity and the specific properties of such a product. This illustrates the extraordinary quality of the product obtained according to the invention, which product is suitable as an emulsifier for fat emulsions used for artificial nutrition and, therefore, meets the extremely high quality standards.

The invention will be explained in greater detail below with reference to examples.

The percentages indicated in the examples for egg lecithin, soybean lecithin, ethanol, and water each are based on the total weight of the starting mixture.

EXAMPLE 1

0.45 kg (3%) of an egg lecithin fraction soluble in alcohol (phosphatidylcholine content=70%) were dissolved in 7.05 kg (47%) of ethanol.

7.50 kg (50%) of water were added to this solution to prepare the starting mixture.

The starting mixture from which a precipitate flocculated at once was mixed for 30 minutes at room temperature. The precipitate was separated by centrifuging (3400 r.p.m.).

The centrifuged product was dried. The product obtained was suitable as an emulsifier for fat emulsions intended for artificial feeding by intravenous administration.

The product had a phosphatidylcholine content of 74%.

The mode of operation described could be carried out readily at room temperature (in a range from about 20° C. to 26° C.).

EXAMPLE 2

1.68 kg (8.4%) of an egg lecithin fraction soluble in alcohol were dissolved in 7.44 kg (37.2%) of ethanol, and 10.88 kg (54.4%) of water were added to constitute the starting mixture.

The resulting mixture was filled into an ultrafiltration arrangement. After circulating the starting mixture for 30 minutes in the arrangement, the ultrafiltration was effected.

| Test conditions: | |
| --- | --- |
| module inlet pressure | 5.6 bar |
| module outlet pressure | 3.9 bar |
| flow of concentrate | 4.7 m³/h |
| flow of permeating substance | 42 l/h |
| separation limit of the membrane (mw) | 25000 |
| test temperature | 25° C. |
| duration of test | 17 min. |

In the test the permeating substance was collected separately and thus continuously withdrawn from the arrangement, while the retent circulated in the arrangement. The retaining capacity of the module amounted to 0.98. Upon termination of the test aliquot parts of the retent and of the permeating substance were reduced at 15 torr and 40° C. and subsequently freeze-dried.

The retent thus obtained had an iodine number of 74.0 and a phosphatidylcholine content of 79.0%, whereas the permeating substance contained only 10.9% of phosphatidylcholine. This shows that the fractionating test was successful.

EXAMPLE 3

The mode of operation was the same as in example 2. The starting mixture was: 0.15 kg (0.80%) of an egg lecithin fraction soluble in alcohol, 7.28 kg (39.0%) of ethanol, and 11.22 kg (60.2%) of water.

| Test conditions: | |
| --- | --- |
| module inlet pressure | 6.4 bar |
| module outlet pressure | 6.3 bar |
| flow of concentrate | 1.6 m³/h |
| flow of permeating substance | 12.6 l/h |
| separation limit of the membrane (mw) | 25000 |
| test temperature | 20° C. |
| duration of test | 57 min. |
| retention capacity of the module | 0.91. |

The finishing was the same as with example 2, the entire retent being isolated. The retent which was recovered as a yield of 41.8% (based on the egg lecithin fraction used) had an iodine number of 72.0 and a phosphatidylcholine content of 76.5%, whereas the permeating substance contained 13% of phosphatidylcholine. This demonstrates that the fractionating test was successful.

EXAMPLE 4

The mode of operation was the same as in example 2. The starting mixture was: 0.62 kg (3.10%) of an egg lecithin fraction soluble in alcohol, 9.54 kg (47.75%) of ethanol, and 9.82 kg (49.15%) of water.

| Test conditions: | |
| --- | --- |
| module inlet pressure | 6.4 bar |
| module outlet pressure | 6.2 bar |
| flow of concentrate | 2.0 m³/h |
| flow of permeating substance | 33.6 l/h |
| separation limit of the membrane (mw) | 25000 |
| test temperature | 20° C. |
| duration of test | 55 min. |
| retention capacity of the module | 0.98. |

The finishing was the same as with example 3. The retent which was recovered as a 57.5% yield (based on the egg lecithin fraction used) had an iodine number of 69.8 and a phosphatidylcholine content of 69.9%. The fractionating test was successful.

EXAMPLE 5

The mode of operation was the same as with example 2. The starting mixture was: 0.24 kg (1.2%) of a soybean lecithin fraction soluble in alcohol, 4.62 kg (23.1%) of ethanol, and 15.14 kg (75.7%) of water.

| Test conditions: | |
| --- | --- |
| module inlet pressure | 5.1 bar |
| module outlet pressure | 4.8 bar |
| flow of concentrate | 3.8 m³/h |
| flow of permeating substance | 21 l/h |
| separation limit of the membrane (mw) | 10000 |
| test temperature | 22° C. |
| duration of test | 15 min. |
| retention capacity of the module | 0.92. |

The finishing was the same as with example 2. The retent recovered had an iodine number of 99.8 and a phosphatidylcholine content of 70%. As compared to that, the permeating substance recovered had an iodine number of 51.2 and a phosphatidylcholine content of 20%. The fractionating test was successful.

EXAMPLE 6

The mode of operation was the same as with example 2. The starting mixture was 0.82 kg (4.1%) of a soybean lecithin fraction soluble in alcohol, 8.08 kg (40.4%) of ethanol, and 11.1 kg (55.5%) of water.

| Test conditions: | |
| --- | --- |
| module inlet pressure | 6.8 bar |
| module outlet pressure | 6.4 bar |
| flow of concentrate | 2.0 m³/l |
| flow of permeating substance | 12.6 l/h |
| separation limit of the membrane (mw) | 10000 |
| test temperature | 22° C. |
| duration of test | 30 min. |
| retention capacity of the module | 0.92. |

The finishing was the same as with example 2. The retent recovered had an iodine number of 103 and a phosphatidycholine content of 49.5%. The fractionating test was only slightly successful.

EXAMPLE 7

Cleaning of lecithins, for example soybean lecithin and preparation of pyrogen-free products.

Using the same mode of operation as with example 2 a total of 9 set-ups of 20 kg each were treated. The starting mixtures were: from 2 to 5% of a soybean lecithin fraction soluble in alcohol, from 37 to 93% of ethanol, and from 4 to 35% of water.

| Test conditions: | |
| --- | --- |
| module inlet pressure | 2.6 to 6.2 bar |
| module outlet pressure | 1.6 to 5.4 bar |
| flow of concentrate | 4.6 to 5.5 m³/h |
| flow of permeating substance | 51 to 199 l/h |
| separation limit of the membrane (mw) | 25000 |
| test temperature | 23 to 30° C. |
| retention capacity of the module | 0 to 0.78. |

A pyrogen-free product was obtained in each case.

EXAMPLES 8 TO 22

Under the following conditions soybean lecithin was fractionated with the aid of an ultrafiltration arrangement:

Composition of the solution to be fractionated: A maximum of 15% of a soybean lecithin fraction soluble in alcohol, a maximum of 35% of ethanol or an aliphatic alcohol, and at least 60% of water (ultrafiltration).

Under the following conditions egg lecithin was fractionated with the aid of an ultrafiltration arrangement:

Composition of the solution to be fractionated:

A maximum of 15% of an egg lecithin fraction soluble in alcohol, a maximum of 52% of ethanol or an aliphatic alcohol, and at least 45% of water. Separation limit of the membranes (MW): 25000.

Table 1 below lists the test conditions for treating other starting mixtures containing soybean or egg lecithin by means of ultrafiltration and the results obtained.

TABLE 1

Test conditions and results of treating further soybean and egg lecithin starting mixtures by ultrafiltration

| (example) | type of membrane | starting mixture composition alcohol | starting mixture composition lecithin % | starting mixture composition lecithin kind | starting mixture composition water % | test data of equipment used T °C. | test data of equipment used P. in bar | test data of equipment used P. out bar | test data of equipment used ΦP bar | test data of equipment used KFl m³/h | test data of equipment used PFl l/h | retention capacity | lecithin concentration R(%) | lecithin concentration P(%) | data JZ R | data JZ P | data POZ R | data POZ P | data H₂O R(%) | data H₂O P(%) | PC—content R(%) | PC—content P(%) |
|---|---|---|---|---|---|---|---|---|---|---|---|---|---|---|---|---|---|---|---|---|---|---|
| 8 | GR | EtOH | 3.9 | soybean | 38.9 | 23 | 6 | 5 | 5.5 | 4.7 | 93 | 0.78 | 4.6 | 1.1 | 92.6 | 75.4 | | | | | | |
| 9 (6) | 6P | | 4.7 | | 18.7 | 26 | 3.4 | 2.5 | 2.9 | 4.7 | 51 | 0.06 | 4.8 | 4.5 | 99.4 | 93.9 | | | | | | |
| 10 (6) | separation limit | | 3.4 | | 4.0 | 26 | 2.6 | 1.6 | 2.1 | 5.5 | 199 | 0 | 3.4 | 3.4 | 94.7 | 94.7 | | | | | | |
| 11 (6) | of membranes: | | 2.3 | | 30.6 | 27 | 4.5 | 3.6 | 4.0 | 5.4 | 76 | 0.25 | 2.4 | 1.8 | 93.9 | 93.5 | | | | | | |
| 12 (6) | 25000 | | 3.6 | | 30.7 | 23 | 6.2 | 5.4 | 5.8 | 4.6 | 110 | 0.62 | 6.9 | 2.6 | 97.3 | 92.6 | | | | | | |
| 12a (6) | | | 2.7 | | 34.6 | 25 | 5.7 | 4.8 | 5.2 | 4.8 | 72 | 0.41 | 2.9 | 1.7 | 93.9 | 88.0 | | | | | | |
| 14b | | | 2.6 | | 36.4 | 26 | 5.7 | 4.8 | 5.2 | 4.8 | 85 | 0.44 | 2.9 | 1.6 | 95.6 | 82.5 | | | | | | |
| 15 | | | 4.8 | | 43.9 | 28 | 5.8 | 4.8 | 5.3 | 4.6 | 93 | 0.40 | 3.2 | 1.9 | 94.1 | 89.0 | | | | | | |
| 16 | | | 3.5 | | 43.6 | 30 | 4.6 | 3.5 | 4.0 | 5.0 | 80 | 0.76 | 5.5 | 1.3 | 101.7 | 82.0 | | | | | | |
| 17 | | i-Pr—OH | 3.5 | | 33.9 | 24 | 5.2 | 3.8 | 4.5 | 4.2 | 76 | 0.29 | 4.1 | 2.9 | 97.0 | 93.0 | | | | | | |
| 18 | | | 2.8 | | 38.7 | 24 | 3.8 | 2.2 | 3.0 | 4.4 | 51 | 0.56 | 3.9 | 1.7 | 96.0 | 93.0 | | | | | | |
| 19 (2) | | EtOH | 8.4 | egg | 54.4 | 25 | 5.6 | 3.9 | 4.7 | 4.7 | 42 | 0.98 | 28.5 | 0.5 | 74.0 | 30 | | | 1.07 | | 79 | 10.9 |
| 20 | | | 8.9 | | 48.3 | 24 | 5.4 | 3.8 | 4.6 | 4.6 | 97 | 0.98 | 16.3 | 0.4 | 71.2 | | | | | | | |
| 21 (5) | GR | EtOH | 1.2 | soybean | 75.7 | 22 | 5.1 | 4.8 | 4.9 | 3.8 | 21 | 0.92 | 1.8 | 0.1 | 99.8 | 51.2 | 3.8 | | | | 70 | 20 |
| 22 | 8P | | 3.6 | | 55.7 | 29 | 7.9 | 7.6 | 7.7 | 3.0 | 17 | 0.86 | 3.7 | 0.5 | 90.1 | 53.3 | | | | | | |
| | TGM: 10000 | | | | | | | | | | | | | | | | | | | | | |

T = test temperature;
P. in = module inlet pressure;
P. out = module outlet pressure;
KFl = concentrate flow;
PFl = permeate flow;
JZ = iodine number;
R = retent;
P = permeating substance;
PC = phosphatidylcholine;
TGM = separation limit of membranes Various modifications in structure and/or function, process steps and/or constituents may be made by one skilled in the art without departing from the scope of the invention as defined by the claims.

What is claimed is:

1. A process for producing an emulsifier from lecithin base by solvent extraction, comprising treating a phospholipid mixture which contains phosphatidylcholine (Pc) and phosphatidylethanolamine (Pe) dissolved in alcohol with sufficient water to cause the partial precipitation of undissolved components of the phospholipid mixture whereafter said components are separated and dried.

2. A process as claimed in claim 1, wherein the amount of water added is so selected that the ratio between Pc and Pe in the separated undissolved proportion is between 7:3 and 6:1, and that the Pc content is at least 5% higher than in the phospholipid starting mixture.

3. A process as in claim 1 wherein the maximum fat content of the phospholipid starting mixture is 2% and the maximum fat content of the phospholipid fraction obtained is 3%, preferably 2%.

4. A process as claimed in claim 1 wherein the separation of the phospholipid fraction which is undissolved after the addition of water is effected by filtration, preferably ultrafiltration such that the undissolved proportions remain in the material retained by the filter or the retent.

5. A process as claimed in claim 1 wherein the separation from the solution of the phospholipid fraction which is undissolved after the addition of water is effected by gravity.

6. A process as in claim 1 wherein drying is effected in vacuum, excluding oxygen, preferably by freeze-drying.

7. A process as in claim 1, wherein egg lecithin dissolved in alcohol is mixed with water in an amount of approximately 35 to 65%, based on the resulting solvent mixture, and the undissolved phospholipid fraction thus precipitated is recovered and dried.

8. A process as in claim 1, wherein soybean lecithin dissolved in alcohol is mixed with water in an amount of from 65 to 96%, based on the resulting solvent mixture, and the undissolved phospholipid fraction thus precipitated is recovered and dried.

9. A process as in claim 1 wherein there is added from 5 to 65% of water, based on the resulting solvent mixture, to the alcoholic solution of egg lecithin and recovering by precipitation the fraction after a period of about 12 to 24 hours.

10. A process as in claim 1 wherein there is added from 5 to 55% of water, based on the resulting solvent mixture, to soybean lecithin dissolved in alcohol, and recovering by precipitation the undissolved phospholipid fraction after a period of about 12 to 24 hours.

11. A process as in claim 1, wherein the alcohol employed is an aliphatic $C_1$ to $C_4$ alcohol, preferably ethanol or isopropanol.

12. An emulsifier having the following physicochemical parameters:
    (1) ratio between Pc and Pe from 7:3 to 6:1, preferably 4:1,
    (2) Pc content from 65 to 85% by weight, preferably from 75 to 80% by weight,
    (3) residual fat content less than 2%,
    (4) pyrogen-free in the rabbit test according to the European Pharmacopoeia (1975) vol. 2, page 56 et seqq.,
    (5) clearly soluble in ethanol at 5% concentration,
    (6) clearly soluble in chloroform at 10% concentration,
    (7) maximum water content 2.5%, preferred maximum 1%,
    (8) maximum peroxide number 5, preferred maximum 1 (determined according to the DGF standard method F-1 3b (68).

* * * * *